United States Patent [19]
Giesecke et al.

[11] 4,110,318
[45] Aug. 29, 1978

[54] POLYPARABANIC ACID DERIVATIVES

[75] Inventors: Henning Giesecke, Cologne; Jürgen Hocker, Bergisch Gladbach; Rudolf Merten, Leverkusen, all of Germany

[73] Assignee: Bayer Aktiengesellschaft, Germany

[21] Appl. No.: 804,606

[22] Filed: Jun. 8, 1977

[30] Foreign Application Priority Data

Dec. 1, 1976 [DE] Fed. Rep. of Germany ....... 2654347

[51] Int. Cl.$^2$ .............................................. C08L 39/04
[52] U.S. Cl. ..................................... 528/73; 548/307; 548/310

[58] Field of Search ................... 260/77.5 CH, 77.5 C, 260/77.5 R; 548/307, 310

[56] References Cited

U.S. PATENT DOCUMENTS

| 3,345,334 | 10/1967 | Angelo | 260/77.5 CH |
| 3,732,185 | 5/1973 | Hocker et al. | 260/77.5 CH |
| 3,933,758 | 1/1976 | Patton | 260/77.5 R |

*Primary Examiner*—M. J. Welsh
*Attorney, Agent, or Firm*—Connolly and Hutz

[57] ABSTRACT

New polyparabanic acid derivatives and their production by reacting $\Delta^2$-imidazolines with organic polyisocyanates.

7 Claims, No Drawings

POLYPARABANIC ACID DERIVATIVES

This invention relates to polyparabanic acid derivatives and to a process for their preparation.

Polyparabanic acid derivatives according to the invention contain the structural unit represented by the following formula (I)

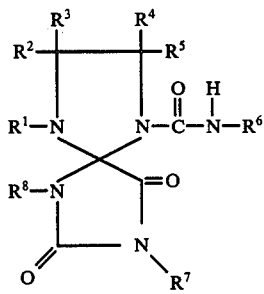

repeated in the molecule, preferably from 2-100 times. In the above formula (I)

$R^1$, $R^6$, $R^7$ and $R^8$ may be the same or different and each represents an optionally substituted aliphatic, aromatic or aliphatic-aromatic group and $R^2$, $R^3$, $R^4$ and $R^5$ may be the same or different and each represents hydrogen or an optionally substituted aliphatic, aromatic or aliphatic-aromatic group. The repeating units represented by formula (I) are linked by the groups, $R^6$ and/or $R^7$ and/or $R^8$.

The monofunctional, difuctional or polyfunctional radicals $R^6$, $R^7$ and $R^8$ are preferably derived from optionally substituted aliphatic radicals having from 2-20, preferably from 2-12 C-atoms, e.g. alkyl radicals having from 2-12 C-atoms, optionally substituted aromatic radicals having from 6-20, preferably from 6-16 C-atoms, e.g. aryl radicals having up to 20 carbon atoms, such as phenyl, naphthyl, diphenyl or diaryl ether radicals, radicals derived from alkyl or aryl esters of organic or inorganic acids, or optionally substituted aliphatic-aromatic radicals having from 7-20 C-atoms, e.g. xylidene.

$R^2$, $R^3$, $R^4$ and $R^5$ are preferably hydrogen or derived from optionally substituted aliphatic radicals having from 1-20, preferably from 1-12 C-atoms, e.g. alkyl radicals having from 1-6 carbon atoms, cycloalkylene groups having from 5-7 carbon atoms, optionally substituted aromatic radicals having from 6-20, preferably from 6-16 C-atoms, e.g. aryl groups such as phenyl, naphthyl, diphenyl or diphenyl ether groups, or optionally substituted aliphatic-aromatic radicals having from 7-20 C-atoms, e.g. benzyl. $R^2$ and $R^3$ or $R^4$ and $R^5$ may also be joined together to form a cycloaliphatic ring.

$R^1$ is derived from an optionally substituted aliphatic radical having from 1-20, preferably from 1-12 C-atoms, e.g. from an alkyl radical having from 1-6 carbon atoms, cycloalkyl radical having from 5-7 carbon atoms in the ring, an optionally substituted aromatic radical having from 6-20, preferably from 6-16, carbon atoms, e.g. aryl groups such as phenyl, naphthyl, diphenyl or diphenyl ether groups, or an optionally substituted aliphatic-aromatic radical having from 7-20 C-atoms, e.g. benzyl radical.

The following are examples of possible substituents of the above mentioned aliphatic, aliphatic-aromatic or aromatic radicals: $C_6$-$C_{16}$ aryl groups (preferably phenyl), OH, aldehyde and ketone groups, CN, $NO_2$, alkylmercapto and alkoxy groups preferably having from 1-4 C-atoms, carboxylic acid ester groups, phosphonic acid ester groups, phosphinic acid ester groups and sulphonic acid ester groups, preferably those obtained from lower aliphatic alcohols, particularly alcohols having from 1-8, more particularly from 1-4 C-atoms; a disubstituted amino group, a disubstituted carboxamide group and a disubstituted sulphonamide group, preferably substituted by lower aliphatic groups (preferably with 1-4 C-atoms), halogens (preferably fluorine, chlorine, or bromine), lower haloalkyl groups (preferably having from 1-4 C-atoms and preferably containing fluorine and/or chlorine) and, in the case of aromatic and heterocyclic radicals, the substituents may also be lower alkyl groups, preferably with 1-4 C-atoms.

The polyparabanic acid derivatives according to the invention preferably have molecular weights of from 1000–50,000, in particular from 4000–30,000 (determined by the osmotic method). They show characteristic IR absorption bands at 1720–1740 cm$^{-1}$ (strong) and 1770–1800 cm$^{-1}$ (weak) in addition to urea carbonyl bands at 1630–1700 cm$^{-1}$ (strong).

A further object of the present invention is a process for the production of the inventive polyparabanic acid derivatives by reacting $\Delta^2$-imidazolines corresponding to the following general formula (II)

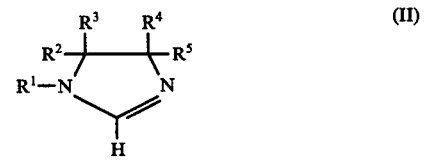

wherein
$R^1$ to $R^5$ are as defined above, with organic polyisocyanates.

The following $\Delta^2$-imidazolines are preferably used for carrying out the process:
1-methyl-$\Delta^2$-imidazoline;
1-ethyl-$\Delta^2$-imidazoline;
1-isopropyl-$\Delta^2$-imidazoline;
1-n-butyl-$\Delta^2$-imidazoline;
1-cyclohexyl-$\Delta^2$-imidazoline;
1-benzyl-$\Delta^2$-imidazoline;
1-phenyl-$\Delta^2$-imidazoline;
1,4-dimethyl-$\Delta^2$-imidazoline;
1-n-butyl-4-methyl-$\Delta^2$-imidazoline;
1-benzyl-5-ethyl-$\Delta^2$-imidazoline;
1,4-diphenyl-$\Delta^2$-imidazoline;
N-(n-butyl)-hexahydrobenzimidazole;
1-cyanoethyl-$\Delta^2$-imidazoline;
3-[1-(2-imidazolinyl)]-propionic acid methyl ester;
3-[1-(2-imidazolinyl)]-propionic acid ethyl ester;
2-[1-(2-imidazolinyl)]-ethylphosphonic acid dimethyl ester;
2-[1-(2-imidazolinyl)]-ethylphosphonic acid diethyl ester;
1-(2-hydroxyethyl)-$\Delta^2$-imidazoline;
1-[3-(3,5-dihydrothiphene-S-dioxid-yl)]-$\Delta^2$-imidazoline;
1-phenyl-4,4-dimethyl-$\Delta^2$-imidazoline; and
1-methoxycarbonylethyl-hexahydrobenzimidazole Organic polyisocyanates for the purpose of the present invention are organic isocyanates having at least two isocyanate groups per molecule.

The polyisocyanates used as starting components according to the present invention may be aliphatic isocyanates having from 2-20 C-atoms, cycloaliphatic isocyanates having from 5-12 C-atoms, arylaliphatic isocyanates having from 7-20 C-atoms, aromatic isocyanates having from 6-20 C-atoms, and heterocyclic isocyanates having from 4-20 C-atoms, for example the polyisocyanates described by W. Siefken in Justus Liebigs Annalen der Chemie, 562 pages 75 to 136. The following are specific examples: ethylene diisocyanate, 1,4-tetramethylene diisocyanate, 1,6-hexamethylene diisocyanate, 1,12-dodecane diisocyanate, cyclobutane-1,3-diisocyanate, cyclohexane-1,3- and 1,4-diisocyanate and any mixtures of these isomers, 1-isocyanato-3,3,5-trimethyl-5-isocyanato methyl-cyclohexane (German Auslegeschrift No. 1,202,785), 2,4- and 2,6-hexahydrotolylene diisocyanate and any mixtures of these isomers, hexahydro-1,3- and/or 1,4-phenylene diisocyanate, perhydro-2,4'- and/or -4,4'-diphenylmethane diisocyanate, 1,3- and 1,4-phenylene diisocyanate, 2,4- and 2,6-tolylene diisocyanate and any mixtures of these isomers, diphenylmethane-2,4'- and/or -4,4'-diisocyanate, naphthylene-1,5-diisocyanate, triphenylmethane-4,4',4"-triisocyanate, polyphenyl-polymethylene polyisocyanate obtainable by aniline-formaldehyde condensation followed by phosgenation, for example the compounds described in British Pat. Nos. 874,430 and 848,671, perchlorinated aryl polyisocyanates such as those described in German Auslegeschrift No. 1,157,601, polyisocyanates containing carbodiimide groups as described in German Pat. No. 1,092,007, the diisocyanates described in U.S. Pat. No. 3,492,330, polyisocyanates containing allophanate groups, e.g. as described in British Pat. No. 994,890, Belgian Pat. No. 761,626 and published Dutch Patent Application No. 7,102,524, polyisocyanates containing isocyanurate groups as described, for example, in German Pat. Nos. 1,022,789, 1,222,067 and 1,027,394 and in German Offenlegungsschrift Nos. 1,929,034 and 2,004,048, polyisocyanates containing urethane groups, e.g. as described in Belgian Pat. No. 752,261 or in U.S. Pat. No. 3,394,164, polyisocyanates containing acylated urea groups according to German Pat. No. 1,230,778, polyisocyanates containing biuret groups, e.g. as described in German Pat. No. 1,101,394, in British Pat. No. 889,050 and in French Pat. No. 7,017,514, polyisocyanates prepared by telomerisation reactions, e.g. as described in Belgian Pat. No. 723,640, polyisocyanates containing ester groups, e.g. the compounds mentioned in British Pat. Nos. 956,474 and 1,072,956, U.S. Pat. No. 3,567,763 and German Pat. No. 1,231,688, and reaction products of the above mentioned isocyanates with acetals according to German Pat. No. 1,072,385.

The distillation residues obtained from the commercial production of isocyanates which still contain isocyanate groups may also be used, optionally in the form of solutions in one or more of the above mentioned polyisocyanates. Any mixtures of the above mentioned polyisocyanates may also be used.

As a rule, it is particularly preferred to use commercially readily available polyisocyanates such as 2,4- and 2,6-tolylene diisocyanate and any mixtures of these isomers ("TDI"), polyphenyl-polymethylene polyisocyanates which are obtained by aniline-formaldehyde condensation followed by phosgenation ("crude MDI") and polyisocyanates containing carbodiimide, urethane, allophanate, isocyanurate, urea or biuret groups ("modified polyisocyanates").

Aliphatic or aromatic monoisocyanates may be used in addition to polyisocyanates to reduce the degree of cross linking of the polyparabanic acid derivatives.

The process is preferably carried out by reacting the starting materials in an organic solvent at temperatures of from $-20°$ to $400°$ C. The polymer produced by the reaction either stays in solution or precipitates. It may be isolated by distillation of the solvent. The quantities of the starting materials may be chosen to provide 0.5 to 10 mol, preferably about 3 mol of isocyanate groups per mol of $\Delta^2$-imidazoline. Solvents suitable for the process are compounds which are inert towards isocyanate groups, for example aromatic hydrocarbons, chlorinated aromatic hydrocarbons, benzonitrile, aliphatic hydrocarbons, esters and ketones. Particularly preferred are toluene, xylene, mesitylene, chlorobenzene, dichlorobenzene, N-methyl pyrrolidone, dimethylformamide, dimethylacetamide, hexamethyl phosphoric acid triamide, tetramethyl urea, nitromethane and nitrobenzene. The compounds may, however, be reacted without solvents.

The reaction times are generally from 15 minutes to 100 hours, preferably from 30 minutes to 20 hours, but may lie above or below these limits in special cases.

Reaction temperatures from $-20°$ to $400°$ C are employed, depending on the particular starting materials. Temperatures from $60°$ to $350°$ C are preferred, particularly from $80°$ to $250°$ C.

Polymerisation may be carried out with the aid of the usual acid or basic catalysts, e.g. metal alcoholates or tertiary amines.

The polyparabanic acid derivatives obtained may carry isocyanate end groups so that they can be cross linked with the usual substances used in isocyanate chemistry, such as polyols or polyamines or they may be cross linked to form isocyanurate structures. Chain lengthening with formation of carbodiimide or uretdione structures is also possible.

Other polymers may also be included in the process of the present invention in known manner, for example polyesters, polyethers, polyamides, polyurethanes, polyolefins, polyacetals, polyepoxides, polyimides, polyamidines, polyimide diisocyanates, and polyhydantoins. These polymers may be added to the finished inventive polymers or they may be copolymerized with them.

According to one special embodiment of the process, polyesters or polyethers containing hydroxyl groups are also added and excess quantities of isocyanate components are used. This results in the formation of a combination of parabanic acid and urethane. For this purpose, mixtures of, for example, polyhydroxyl compounds, polyisocyanates or derivatives thereof and a compound of the general formula (II) are converted simultaneously in a final step of the process into the synthetic resin, optionally after precondensation of two of these components.

The hydroxyl polyesters used are commonly known and obtained in the usual manner from polycarboxylic acids such as succinic, adipic, sebacic, phthalic, isophthalic, terephthalic or oleic acids and polyhydric alcohols such as glycol, diethylene glycol, triethylene glycol, propylene glycol, dipropylene glycol, glycerol, trimethylolpropane or pentaerythritol.

The polyparabanic acid derivatives according to the invention and mixtures thereof with other polymers are temperature resistant synthetic resins which have excellent mechanical properties and may be used as lacquers and foils, etc. They may contain the usual additives used for synthetic resins, such as fillers, pigments, anti-oxidants and plasticisers.

EXAMPLE 1

17.4 parts by weight of 2,4-tolylene diisocyanate were added dropwise to 6.3 parts by weight of 1-(n-butyl)-$\Delta^2$-imidazoline in 20 parts by weight of dichlorobenzene at 30° C over a period of 1 hour. The reaction mixture was then stirred at 160° C for 1 hour. 18.0 parts by weight of a solid polymer were obtained after filtration. This polymer has the characteristic IR absorption bands for parabanic acid derivatives at 1787 cm$^{-1}$ (weak) and 1729 cm$^{-1}$ (strong).

EXAMPLE 2

12.3 parts by weight of 1-cyanoethyl-$\Delta^2$-imidazoline were added dropwise to 26.1 parts by weight of an isomeric mixture of 80 parts of 2,4-tolylene diisocyanate and 20 parts of 2,6-tolylene diisocyanate in 40 parts by weight of dimethylformamide at 60° C within a period of 1 hour. The reaction mixture was then stirred for 1 hour at 100° C. 38 parts by weight of a solid polymer were obtained after filtration. Viscosity of a 38% solution in m-cresol at 25° C: 23280 cP.

EXAMPLE 3

4.0 parts by weight of 1-benzyl-$\Delta^2$-imidazoline and 12.2 parts by weight of diphenylmethane-diisocyanate-(4,4') were stirred into 20 parts by weight of toluene at 110° C over 30 minutes. 13.6 parts by weight of a solid polymer were obtained by filtration. The polymer has the characteristic IR absorption bands for parabanic acid derivatives at 1788 cm$^{-1}$ (weak) and 1730 cm$^{-1}$ (strong).

EXAMPLE 4

7,8 parts by weight of 3-[1-(2-imidazolinyl)]-propionic acid methyl ester were added dropwise within 1 hour to 17.4 parts by weight of 2,4-tolylene diisocyanate in 20 parts by weight of toluene at 100° C. 24.6 parts by weight of a solid polymer were obtained after filtration. Viscosity of a 33% solution in cresol at 25° C: 3360 cP.

EXAMPLE 5

12.3 parts by weight of 1-cyanoethyl-$\Delta^2$-imidazoline were added dropwise to 44.4 parts by weight of isophorone diisocyanate within 1 hour at 100° C. The reaction mixture was then stirred for 1 hour at 150° C. After dehydration under vacuum, 50.2 parts by weight of a solid polymer containing isocyanate groups were obtained. The polymer had the characteristic IR absorption bands for parabanic acid derivatives at 1777 cm$^{-1}$ (weak) and 1718 cm$^{-1}$ (strong). Viscosity of a 33% solution in cresol at 25° C: 11040 cP.

EXAMPLE 6

5.7 parts by weight of 1-(2-hydroxyethyl)-$\Delta^2$-imidazoline in 30 parts by weight of chloroform were added dropwise to 22.2 parts by weight of isophorone diisocyanate within 1 hour at 60° C. The resulting solution was evaporated under vacuum and dried. 27.1 parts by weight of a solid polymer having the characteristic IR absorption bands for parabanic acid derivatives at 1776 cm$^{-1}$ and 1728 cm$^{-1}$ (strong) were obtained. Average molecular weight determined by the GPC method in tetrahydrofuran: 1850.

EXAMPLE 7

5.9 parts by weight of 2,5-dihydrothiophene-S-dioxide in 60 parts by weight of chloroform were added dropwise to 3.5 parts by weight of $\Delta^2$-imidazoline at 50° C within 1 hour. The reaction mixture was then stirred for 30 minutes at 60° C and 12.6 parts by weight of 2,4-tolylene diisocyanate were then added dropwise at this temperature over a period of 30 minutes. The reaction mixture was then stirred for 1 hour at 60° C. 16.9 parts by weight of a solid polymer were obtained after filtration and drying under vacuum. Viscosity of a 33% solution in N-methyl pyrolidone at 25° C: 140 cP.

EXAMPLE 8

6.8 parts by weight of vinyl phosphonic acid dimethyl ester were added dropwise within 1 hour to a suspension of 3.5 parts by weight of $\Delta^2$-imidazoline in 10 parts by weight of toluene at room temperature. 26.1 parts by weight of an isomeric mixture of 80 parts by weight of 2,4-tolylene diisocyanate and 20 parts by weight of 2,6-tolylene diisocyanate in 10 parts by weight of toluene were then added dropwise over a period of 6 hours. The solution was heated to 110° C for 10 minutes. 28.9 parts by weight of a solid polymer were thereby precipitated. The polymer was suction filtered and dried under vacuum.

EXAMPLE 9

15.6 parts by weight of 3-[1-(2-imidazolinyl)]-propionic acid methyl ester were added dropwise to 134.4 parts by weight of hexamethylene diisocyanate within 1 hour at 80° C. Stirring was continued for 1 more hour at 80° C. Evaporation of the solution under a high vacuum at 150° C yielded 66 parts by weight of a prepolymer containing 14.2% of isocyanate groups. Viscosity of a 75% solution in ethylene glycol monomethyl ether acetate at 25° C: 2400 cP.

50 parts by weight of this 75% solution of the prepolymer were mixed with 40 parts by weight of a 65% solution in ethyl glycol acetate of a polyester which had been prepared from 52 parts by weight of phthalic acid anhydride, 0.6 parts by weight of maleic acid anhydride and 54 parts by weight of trimethylol propane and contained 5.2% of hydroxyl groups, and 0.1 part by weight of Sn(II) dioctoate. A quick drying lacquer was obtained.

EXAMPLE 10

8.7 parts by weight of 4,4-dimethyl-1-phenyl-$\Delta^2$-imidazoline were added dropwise within 1 hour to 12.6 parts by weight of hexamethylene diisocyanate in 30 parts by weight of chloroform at 60° C. When the solution was concentrated by evaporation under vacuum, 18.1 parts by weight of a solid polymer which had the characteristic IR absorption bands for parabanic acid derivatives at 1779 cm$^{-1}$ (weak) and 1722 cm$^{-1}$ (strong) were obtained.

What is claimed is:

1. Polyparabanic acid derivatives which contain the following recurring structural unit from 2 to 100 times

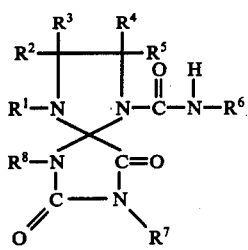

wherein $R^1$, $R^6$, $R^7$ and $R^8$ may be the same or different, and each represents an optionally substituted aliphatic, aliphatic-aromatic or aromatic radical, and $R^2$, $R^3$, $R^4$ and $R^5$ may be the same or different, and each represents hydrogen or an optionally substituted aliphatic, aliphatic-aromatic or aromatic radical.

2. Polyparabanic acid derivatives as claimed in claim 1 which have a molecular weight of from 1,000 to 50,000.

3. Polyparabanic acid derivatives as claimed in claim 1, wherein $R^1$, $R^6$, $R^7$ and $R^8$ may be the same or different, and each is an optionally substituted aliphatic radical containing from 2 to 20 carbon atoms or an optionally substituted aromatic radical containing 6 to 20 carbon atoms and $R^2$, $R^3$ $R^4$ and $R^5$ may be the same or different and are each hydrogen or one of said moieties defining $R^1$, $R^6$, $R^7$ and $R^8$.

4. A process for the preparation of polyparabanic acid derivatives as claimed in claim 1 wherein a $\Delta^2$-imidazoline of the formula

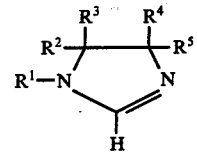

wherein $R^1$ to $R^5$ are as defined in claim 1 is reacted with an organic polyisocyanate at a temperature of from $-20°$ to $400°$ C.

5. A process as claimed in claim 4 wherein the reaction is carried out at a temperature of from $60°$ to $350°$ C.

6. A process as claimed in claim 5 wherein the reaction is carried out at a temperature of from $80°$ to $250°$ C.

7. A process as claimed in claim 4 wherein the reaction is carried out using from 0.5 to 10 moles of isocyanate per mole of $\Delta^2$-imidazoline.

* * * * *